US008557606B2

(12) United States Patent
Meinhardt et al.

(10) Patent No.: US 8,557,606 B2
(45) Date of Patent: Oct. 15, 2013

(54) IMMUNOLOGICAL TEST FOR DETECTING AUTOANTIBODIES AGAINST TESTICULAR ANTIGENS

(75) Inventors: Andreas Meinhardt, Marburg (DE); Monika Fijak, Marburg (DE)

(73) Assignee: Justus-Liebig-Universitat Giessen, Giessen (DE)

( * ) Notice: Subject to any disclaimer, the term of this patent is extended or adjusted under 35 U.S.C. 154(b) by 0 days.

(21) Appl. No.: 13/126,429

(22) PCT Filed: Oct. 22, 2009

(86) PCT No.: PCT/EP2009/063878
§ 371 (c)(1),
(2), (4) Date: Jul. 18, 2011

(87) PCT Pub. No.: WO2010/049340
PCT Pub. Date: May 6, 2010

(65) Prior Publication Data
US 2011/0269157 A1    Nov. 3, 2011

(30) Foreign Application Priority Data

Oct. 28, 2008 (DE) .......................... 10 2008 053 503

(51) Int. Cl.
*G01N 33/543* (2006.01)

(52) U.S. Cl.
CPC .................................. *G01N 33/543* (2013.01)
USPC ............ 436/518; 435/7.1; 435/7.92; 436/501

(58) Field of Classification Search
None
See application file for complete search history.

(56) References Cited

U.S. PATENT DOCUMENTS

2011/0243928 A1* 10/2011 Ashman et al. ............ 424/133.1
2012/0040356 A1*  2/2012 Hussa et al. ................. 435/6.12
2012/0122723 A1*  5/2012 Taylor et al. ..................... 506/9

FOREIGN PATENT DOCUMENTS

WO    WO 2006/046108 A2    5/2006

OTHER PUBLICATIONS

Yasuoka et al., Autoantibody response against a novel testicular antigen protein highly expressed in testis in SSc patients, Autoimmun Rev. 2007, Mar. 6(4) pp. 228-231.*
Bohring et al., Isolation and identification of sperm membrane antigens recognized by antisperm antibodies, and their possible role in immunological infertiltiy disease, Molecular Human Reproducion vol. 7, No. 2, pp. 113-118, 2001.*
Moore, Elaine, Causes of Infertility, Autoimmune Interfility May 2006, pp. 1-5.*
Bohring et al., "Isolation and identification of sperm membrane antigens recognized by antisperm antibodies, and their possible role in immunological infertility disease," *Molecular Human Reproduction*, 7(2):113-118 (2001).
German Office Action for 10 2008 053 503.6-52, dated Oct. 23, 2009.
Fijak et al., "Identification of immunodominant autoantigens in rat autoimmune orchitis," *Journal of Pathology*, 207:127-138 (2005).
International Search Report for PCT/EP2009/063878, dated Feb. 9, 2010.
Mathur, "Autoimmunity in Endometriosis: Relevance to Infertility," *American Journal of Reproductive Immunology*, 44:89-95 (2000).
Seignaurin et al., "Polyspecific Natural Antibodies and Autoantibodies Secreted by Human Lymphocytes Immortalized With Epstein-Barr Virus," *Blood*, 71(3):581-585 (1988).
Zhang et al., "ERp57 is a potential biomarker for human fertilization capability," Molecular Human Reproduction 13(9): 633-639 (2007).

* cited by examiner

*Primary Examiner* — Gary W Counts
(74) *Attorney, Agent, or Firm* — Marshall, Gerstein & Borun LLP

(57) ABSTRACT

The present invention discloses an immunological test for the detection and specific determination of autoantibodies against testicular antigens which are associated with inflammation-related fertility disorders of male mammals in a biological sample of a male mammal, in particular the detection of testicular ER-60 autoantibodies and/or transferrin autoantibodies. The immunological test is utilized to detect the presence of immunologically-caused and infection-related infertility in male mammals, particularly in humans.

5 Claims, No Drawings

SEQUENCE LISTING

```
<160> NUMBER OF SEQ ID NOS: 1

<210> SEQ ID NO 1
<211> LENGTH: 1444
<212> TYPE: DNA
<213> ORGANISM: Homo sapiens
<300> PUBLICATION INFORMATION:
<301> AUTHORS: URADE, R., NASU, M., MORIYAMA, T., WADA, K., AND KITO, M.
<302> TITLE: Protein degradation by the phosphoinositidespecific
      phospholipase Calpha family from rat liver endoplasmic reticulum
<303> JOURNAL: Journal of Biological Chemistry
<304> VOLUME: 267
<305> ISSUE: 1992
<306> PAGES: 15152-15159
<307> DATE: 1992
<313> RELEVANT RESIDUES IN SEQ ID NO: (1)..(1444)

<400> SEQUENCE: 1
atgtccgacg tgctagaact cacggacgac aacttcgaga gtcgcatctc cgacacgggc      60
tctgcgggcc tcatgctcgt cgagttcttc gccccctggt gtggacactg caagagactt     120
gcacctgagt agaagctgca gctaccagat taaaaggaat agtcccatta gcaaaggttg     180
attgcactgc caacactaac acctgtaata aatatggagt cagtggatat ccaaccctga     240
agatatttag agatggtgaa gaagcaggtg cttatgatgg acctaggact gctgatggaa     300
ttgtcagcca cttgaagaag caggcaggac cagcttcagt gcctctcagg actgaggaag     360
aatttaagaa attcattagt gataaagatg cctctatagt aggtttttc gatgattcat      420 tcagtgaggc tcactccgag ttcctaaaag cagccagcaa cttgagggat aactaccgat     480
ttgcacatac gaatgttgag tctctggtga acgagtatga tgataatgga gagggtatca     540
tcttatttcg tccttcacat ctcactaaca agtttgagga caagactgtg gcatatacag     600
agcaaaaaat gaccagtggc aaaattaaaa agtttatcca ggaaaacatt tttggtatct     660
gccctcacat gacagaagac aataaagatt tgatacaggg caaggactta cttattgctt     720
```

```
actatgatgt ggactatgaa aagaacgcta aaggttccaa ctactggaga acagggtaat    780
gatggtggca aagaaattcc tggatgctgg gcacaaactc aactttgctg tagctagccg    840
caaaccttta gccatgaact ttctgatttt ggcttggaga gcactgctgg agagattcct    900
gttgttgcta tcagaactgc taaaggagag aagtttgtca tgcaggagga gttctcgcgt    960
gatgggaagg ctctggagag gttcctgcag gattactttg atggcaatct gaagagatac   1020
ctgaagtctg aacctatccc agagagcaag atgggcctgt gaaggtagtg gtagcagaga   1080
attttgatga aatagtgaat aatgaaaata aagatgtgct gattgaattt tatgcccctt   1140
ggtgtggtca ctgtaagaac ctggagccca agtataaaga acttggcgga agctcagcaa   1200
agacccaaat atcgtcatag ccaagatgga tgccacagcc aatgatgtgc cttctccata   1260
tgaagtcaga ggttttccta ccatatactt ctctccagcc aacaagaagc taaatccaaa   1320
gaaatatgaa ggtggccgtg aattaagtga ttttattagc tatctacaaa gagaagctac   1380 aaaccccct gtaattcaag aagaaaaacc caagaagaag aagaaggcac aggaggatct   1440
ctaa                                                                1444
```

IMMUNOLOGICAL TEST FOR DETECTING AUTOANTIBODIES AGAINST TESTICULAR ANTIGENS

The application contains, as a separate part of disclosure, a Sequence Listing in computer-readable format (filename: 46004_SeqListing.txt; 2,755 bytes—ASCII text file) which is incorporated by reference in its entirety.

The present invention relates to an immunological test for the detection of autoantibodies against testicular antigens which were identified as highly relevant for forms of immunologically-caused and infection-related infertility in male mammals.

The test is utilized for the diagnosis and therapeutic control of diseases which are associated with an elevated level of autoantibodies against testicular antigens, such as inflammation-related male fertility disorders like e.g. silent, but also symptomatic inflammations of the testicles and associated male sexual organs.

STATE OF THE ART

Approximately every seventh couple in Germany is affected by involuntary childlessness, whereby the causes are almost equally divided between men and women. On the part of the man, in addition to idiopathic infertility (approx. 30%) also urogenital infections or other immunological factors (altogether approx. 12-15%) are counted among the most important reasons for a limited fertility. As well systemic acute and chronic inflammatory diseases as also local infections and inflammations of the male genital tract play, either alone or as associated cause of male fertility disorders, always an important role. Chronic inflammatory changes in the testicles (testicle inflammation or orchitis) may result in spermatogenic arrest and in substantial alterations of spermatozoa number and -quality. An inflammation of the epididymis (epididymitis) with an estimated annual incidence of e.g. more than 600 000 cases in the USA often appears combined as epididymoorchitis. Of clinical relevance for fertility disorders are also sperm-immobilizing and/or sperm-agglutinating autoantibodies. An assessment of the relevance of immunologically-caused male infertility and the consequences thereof is in particular hampered by the fact that a high number of cases with asymptomatic progression is expected.

The diagnosis of infections of the seminal ducts is dissatisfying, being based upon the detection of pathogens, an increased occurrence of leucocytes and/or inflammation mediators in the ejaculate as well as a reduced secretory activity of the accessory glands. Asymptomatic inflammatory damage of the testes is generally only diagnosable with certainty via testicular biopsy and thus often remains unrecognized as cause or contributing factor of fertility disorders. It is consequently conceivable that inflammations also account for a part of the large patient collective with idiopathic infertility and that inflammatory causes are of higher relevance than previously assumed.

Therefore demand exists for a test suitable to be used in a body fluid or a biological sample for the identification of inflammation-related male fertility disorders such as e.g. silent, but also symptomatic inflammations in testes and associated male sexual organs, in order to reduce the need for a testicular biopsy. Granulocyte elastase and IL-6 are unfortunately both non-specific and thus unsuitable for a utilization as makers. So far, no appropriate marker is known which is suitable for the specific detection of inflammation-related male fertility disorders and thus can be used in an assay.

AIM

Aim of the present invention is to provide a marker which is suitable for the specific detection of inflammation-related male fertility disorders, as well as an easy to perform and non-invasive procedure for the detection of this marker in a biological sample. The aim is furthermore to provide a test kit for carrying out this procedure.

Solution of the Aim

This aim is solved according to the present invention by an immunological test for the detection and specific determination of autoantibodies against testicular antigens which are specific for inflammation-related male fertility disorders in a biological sample, according to the claims.

In own tests surprisingly specific autoantibodies against testicular antigens were identified in biological samples as highly relevant for forms of immunologically-caused infertility in men.

These results demonstrate that biological samples such as e.g. sera from patients with various forms of testicular inflammations very often show high titers of ER-60 autoantibodies and transferrin-antibody titers and thus can be distinguished from healthy test persons or men with non-inflammatory spermatogenic defects (e.g. Sertoli cell-only syndrome, spermatogenic arrest, oligoasthenoterato-zoospermia).

For this purpose, testicle extracts of patients with normal spermatogenesis were separated by 2D-SDS-PAGE, a technique known to the expert, and transferred to nitrocellulose membranes as e.g. disclosed in Journal of Pathology (2005; 207, 127-138). The blot membranes were incubated with control sera from women, from healthy subjects or with serum samples from patients who were after andrological examination diagnosed with various forms of focal or less frequent fully developed inflammation of the testes. Autoreactive spots were investigated using mass spectrometry (MALDI-MS), and proteins were identified against which frequently antibodies were directed in the sera of men with inflammation-related infertility:

| Positive sera/total number of sera (% reactivity) | Protein identified |
|---|---|
| 12/13 (92%) | disulfide isomerase ER-60 (syn. Erp60, ERp57) |
| 8/13 (61%) | transferrin (siderophilin) |

Control sera reacted with none of the identified protein spots.

Surprisingly, the proteins disulfide isomerase ER-60 (synonyms: ERp57, p58, entry name: PDIA3_HUMAN) with 92% and transferrin (siderophilin) with 61%, respectively, both showed a strong specific autoreactivity with sera from patients with different forms of testicular inflammation.

For this reason, proteins disulfide isomerase ER-60 (synonyms: ERp57, p58, entry name: PDIA3_HUMAN) and transferrin (siderophilin) were identified as specific markers for testicular inflammations in male mammals.

Utilizing the nucleic acid sequence and/or amino acid sequences of these marker proteins, an immunological test is provided which allows the specific detection of autoantibodies against testicular antigens, in particular ER-60 autoantibodies and/or transferrin autoantibodies which are associated with inflammatory male fertility disorders, in biological samples.

The immunological test for the detection and specific determination of autoantibodies against testicular antigens which are associated with inflammatory male fertility disorders in a biological sample comprises the binding of autoantibodies against testicular antigens, in particular ER-60 autoantibodies and/or transferrin autoantibodies, to the specific testicular antigen, particularly ER-60 or transferrin.

The test according to the invention is used for the diagnosis and therapeutic control of silent, but also symptomatically progressing inflammations of the testicles and associated sexual organs of male mammals.

The amount of autoantibodies against testicular antigens, in particular ER-60 autoantibodies and/or transferrin autoantibodies which occur very frequently in patients with various forms of testicular inflammations, is for this purpose determined in biological samples from male mammals. The determined content of autoantibodies against testicular antigens is then compared with a reference value.

In a preferred embodiment of the invention, the test according to the invention comprises the determination of the content of ER-60 autoantibodies in biological samples, particularly serum. For this purpose, the testicular antigen, in particular protein ER-60, is provided as marker in recombinant form. This is done on the basis of the nucleic acid sequence of ER-60 protein as specified in Seq ID No. 1 by recombinant means, using generally known molecular-biological methods, e.g. by expression in E. coli and according to the state of the art, e.g. using HPLC purification.

According to the invention, in addition to the nucleic acid sequence of protein disulfide isomerase ER-60 (synonyms: ERp57, p58, entry name: PDIA3_HUMAN) as disclosed in Seq ID No. 1, also proteins are included which resulted from minor alterations of the nucleic acid sequence, from additions, deletions and/or substitutions, provided that the function of the translated protein is not substantially affected by a binding of ER-60 autoantibodies.

According to the present invention, in addition to the disclosed nucleic acid sequence of protein disulfide isomerase ER-60, also synonymous and homologous proteins are included such as e.g.: ERp57, p58, entry name: PDIA3_HUMAN.

A biological sample is any biological material obtained from a mammal, in particular from a human, which contains autoantibodies, e.g. body fluid such as whole blood, serum or plasma, seminal plasma, spinal fluid, peritoneal fluid, saliva, lacrimal fluid or urine, furthermore biopsy material or tissue.

Autoantibodies against testicular antigens present in the biological sample, in particular ER-60 autoantibodies and/or transferrin autoantibodies, are identified by specific binding to the respective testicular antigen, in particular ER-60 protein and transferrin, respectively, and subsequent detection using suitable detection procedures.

According to a preferred embodiment of the invention is the determination of autoantibodies against testicular antigens, in particular the determination of ER-60 autoantibodies and/or transferrin autoantibodies, performed by immunological procedures. Especially immunocytochemical procedures, the determination by radioimmunoassay (RIA) or the determination using an enzyme-linked immunosorbent assay (ELISA) proved to be particularly well suited. Alternatively, the test is arranged on a test carrier with the smallest possible volume requirement, e.g. on a test strip.

Conduction of the immunological test comprises contacting a blood sample or other biological specimen of a male mammal whose content of autoantibodies against testicular antigens is to be determined with adsorbed specific testicular antigen, at least one washing step in order to remove non-adsorbed components, and the detection of autoantibodies bound to the adsorbed antigen using a preparation of IgG antibodies which are species-specific for the male mammal to be investigated and which can bind species-specifically to the autoantibody, e.g. in case of a human, a preparation of anti-human IgG antibodies which is labeled in such a way that these antibodies can be detected using a cascade of reactions of the biotin-streptavidin-peroxidase or -alkaline phosphatase type.

In a preferred embodiment, the test is conducted by immobilizing the marker protein to be bound, in particular the testicular antigen, e.g. protein ER-60 or transferrin, on a surface like for example a microtiter-plate, a polyvinyl chloride plate or a suitable tissue plate or a test strip, and saturation of the non-specific binding sites. The biological sample to be investigated is subsequently added, preferably in liquid form, whereby the autoantibody contained therein binds to the testicular antigen, e.g. ER-60 autoantibodies bind to immobilized ER-60 protein and transferrin autoantibodies bind to immobilized transferrin. The test alternatively also detects ER-60 autoantibodies and transferrin autoantibodies if protein ER-60 or transferrin is immobilized on a surface. After at least one washing step, a secondary antibody is added which binds to the autoantibody against testicular antigens and which is coupled to an enzyme, for example an alkaline phosphatase or peroxidase. After at least one further washing step, a colorless or non-fluorescent substrate of the enzyme coupled to the second antibody is finally added to the sample. This enzyme converts the substrate into a colored or fluorescent product whose concentration can be determined with a suitable detector, e.g. a photometer.

With this immunological ELISA assay, even small amounts of autoantibodies against testicular antigens, particularly ER-60 autoantibodies and/or transferrin autoantibodies, can be detected fast and reliably. A further advantage of this test is that it can be performed with commonly used ELISA devices and commercially available microtiter-plates with 96, 256 or even 1024 wells, thus allowing to perform a large number of analyses at the same time.

In a RIA assay, in principle the same steps are carried out as described for the ELISA assays, with the exception that instead of a second antibody conjugated to a suitable enzyme, a radioactively labeled second antibody is used. The quantitative detection is in this case performed with a scintillation counter.

Apart from the above mentioned procedures, a determination of autoantibodies against testicular antigens by binding to the marker protein, i.e. binding of ER-60 autoantibodies to immobilized protein ER-60 and binding of transferrin autoantibodies to immobilized transferrin, respectively, can also be qualitatively and quantitatively assessed with other immunological methods known to the expert in this field, amongst which only the western-blot procedure and the dot-blot method are mentioned here.

Alternatively is the testicular antigen, in particular protein ER-60 and/or transferrin, applied to a test carrier with the smallest possible volume requirement, e.g. to a test strip with one or several absorbent matrices on a suitable carrier substance, and is then brought into contact with the biological sample, if possible in liquid form, so that the autoantibodies against testicular antigens contained therein can bind and subsequently be detected by suitable detection systems, e.g. by the formation of a visible line.

The qualitative or quantitative detection of autoantibodies against testicular antigens, in particular the binding of ER-60 autoantibodies to immobilized protein ER-60 or the binding of transferrin autoantibodies to immobilized transferrin, is preferably performed in body fluids such as serum or plasma from an individual, whereby as a measure for binding, the fluorescence is determined e.g. as optical density (OD) at a wavelength of 450 and 570 nm. The absorbance value is calculated from the difference between 450 nm and 570 nm wavelength.

This value is compared with a reference value. The reference value is e.g. calculated from measured data of biological samples from healthy male mammals and/or mammals with diagnosed testicular inflammation.

Alternatively a sample with defined concentration of testicular antigen is used, in particular ER-60 or transferrin, and the reference value is for example calculated from reference curves or reference tables or in the form of comparative values which are used as basis.

The reference value is preferably determined in parallel to the analysis of the sample. Double determinations of reference value and sample are alternatively possible. The reference value is for example calculated using measurement data of biological samples from healthy donors, whereby the reference value is in this case preferably below an OD value of 0.35. The reference value is for example calculated using measurement data of biological samples from donors with diagnosed silent or symptomatically progressing testicular inflammation, whereby the reference value in this case is above an OD-value of 0.35, preferably above 0.4.

If the content of autoantibodies against testicular antigens of the biological samples, in particular ER-60 autoantibodies and/or transferrin autoantibodies, is above an OD value of 0.35, preferably above 0.4, is this indicative of the presence of an inflammation-related fertility disorder.

The immunological test allows an improved non-invasive diagnosis, particularly in the case of biological samples from patients with silent or symptomatic inflammatory fertility disorders, and avoids performing a testicular biopsy.

In particular, ER-60 autoantibodies and/or transferrin autoantibodies are detected with the immunological test according to the present invention. This allows to distinguish the diagnosis of testicular inflammations from inflammatory spermatogenesis defects (Sertoli cell-only syndrome). It is a new systematic analysis which also takes into account discrete changes such as disseminated and a low density of lymphocytes. The immunological test according to the present invention is also used to assess the success of a therapy of an inflammation-related fertility disorder.

Since the immunological test according to the invention can easily be standardized, it may be used both in human medicine, in particular in the monitoring of in vitro fertilizations or in fertilization diagnoses and expert opinions, and also within the scope of modern livestock breeding.

The biological sample is according to the invention derived from a male mammal, particularly preferred from a human.

The immunological test according to the invention can easily be offered in the form of a ready-to-use "kit", comprising ER-60 and/or transferrin antigen that is adsorbed to the surface of a carrier, and a preparation of IgG antibodies which are species-specific for the male mammal to be investigated and which can species-specifically bind to the autoantibody, e.g. in case of a human, a preparation of anti-human IgG antibodies labeled in such a way that these can be detected with a cascade of reactions of the biotin-streptavidin-peroxidase or -alkaline phosphatase type.

Alternatively, the kit comprises a carrier and also buffers and reagents, e.g. reagents required for the detection of the reaction like e.g. streptavidin coupled to a marker which results in a color reaction.

Alternatively, the kit additionally comprises a standard sample of ER-60 antibodies or transferrin antibodies for calibrating the kit, whereby a standard sample of ER-60 antibodies is used for the detection of ER-60 autoantibodies and a standard sample of transferrin antibodies is used for the detection of transferrin autoantibodies.

EMBODIMENTS

1. Provision of ER-60

Preferably provided is in *E. coli* expressed recombinant protein disulphide isomerase ER-60 (synonyms: ERp57, p58, entry name: PDIA3_HUMAN). This is for examples done using an expression clone which contains the DNA-sequence of human ER-60, e.g. pET-hER-60 expression clone as e.g. described in Urade et al., J. Biochem. 122, 834-842; 1997. The protein is expressed e.g. in *E. coli* BL21 (DE3), for example according to the protocol of Urade et al. J Biol Chem. 267 (21):15152-15159), and purified e.g. using HPLC.

For this purpose, the expression plasmid pET-hER60 is transformed into *E. coli* BL21(DE3) and cultivated under suitable conditions, e.g. in the presence of ampicillin (500 µg/ml) in 400 ml medium, e.g. LB-medium (1% tryptone, 0.5% yeast extract, 1% NaCl; pH 7.0) at 30° C. Protein expression is induced at a suitable $OD_{600nm}$ value, e.g. at $OD_{600nm}$ value=0.5, e.g. with 0.5 mM iso-propyl-1-thio-β-D-galactopyranoside (IPTG) at 30° C. for approx. 2 h. The bacterial culture is subsequently harvested and the pellet is resuspended in a suitable buffer and precipitated, e.g. resuspended in 10 ml buffer, e.g. 20 mM HEPES-KOH (pH 6.8), 50 mM KCl, 5 mM EDTA (pH 8.0), 1 mM PMSF and sonicated The cell lysate is centrifuged for approx. 30 min at 4° C. at 5 000×g and the supernatant is precipitated with 60 and 70% saturated ammonium sulfate for 30 min at 4° C., followed by centrifugation 5 000×g for 30 min. The protein pellet is resuspended in 500 µl buffer, e.g. 20 mM HEPES-KOH (pH 6.8), 50 mM KCl, 5 mM EDTA (pH 8.0), 1 mM DTT and purified, e.g. using gel filtration (Superdex 200 HR) in HPLC. In an alternative step, those fractions which contain hER-60 are further purified, e.g. using a Mono Q column e.g. in 10 ml buffer, e.g. 20 mM HEPES-KOH (pH 6.8), 50 mM KCl, 5 mM EDTA (pH 8.0), 1 mM DTT. The purity of the protein is assessed, e.g. in an SDS-PAGE gel.

2. Immunological Test

An ELISA plate e.g. MAXISORP (polystyrene) ELISA plate (Nunc) is coated with recombinant ER-60, e.g. 2.5 µg/ml over night at 4° C. in 0.1 M sodium carbonate, pH 9.5, washed with suitable buffer, e.g. phosphate buffer (PBS, pH 7.2+0.05% TWEEN 20 (polysorbate)) and blocked, e.g. with 2% skimmed milk powder in PBS at room temperature (RT) for 2.5 hours. After blocking of unspecific binding sites, dilution series (ranging from undiluted to 1:1 000 dilution in blocking solution) of control samples and serum samples to be tested are each applied to the coated plate in duplicates and incubated for 1 hour at RT. After this incubation time, wells are washed at least once and subsequently incubated for at least one hour at RT with a second species-specific antibody, e.g. an anti-human IgG-biotin (1:100 000 in blocking solution). After at least one washing step, the samples are incubated with streptavidin-horseradish peroxidase (GE Healthcare) 1:4 000 in washing buffer for 20 min at RT. After at least one washing step, the color reaction is developed for 20 min, e.g. with TMB (3,3',5,5'-tetramethylbenzidine; BD Biosciences). The color reaction is stopped, e.g. with 2N $H_2SO_4$. The absorption (OD value) is determined at a wavelength of 450 and 570 nm. The absorption value results from the difference between 450 nm and 570 nm wavelength.

3. Data Analysis

Evaluation of the immunological assay is preferably performed by a quantification of ER-60 autoantibodies in biological samples, preferred serum or plasma. The measured value is compared with a reference value. This reference value is e.g. calculated from measurement data of samples from healthy donors and is in this case preferably lower than an OD value of 0.35. Alternatively, the reference value can be determined from measurement data of samples from donors with diagnosed testicular inflammation, whereby the reference value in this case is above an OD value of 0.35, preferably above 0.4. Alternatively, a sample with defined concentration of ER-60 is used and the reference value is for example calculated from comparison curves or comparison tables or is based upon comparison values. The reference value is preferably determined in parallel to the analysis of the sample.

If the content of ER-60 autoantibodies in the sample is above an OD value of 0.35, preferably above 0.4, is this an indication for the presence of an inflammation-related fertility disorder of the male mammal.

4. Validation

In order to validate the immunological test according to the present invention, extensive test series are conducted, whereby the detection of ER-60 autoantibodies in a control group using sera from humans without andrologically relevant pre-existing conditions and normal ejaculate is compared with different patient groups.

These patient groups consists of:
1. sera from men with limited fertility. Inclusion criterion is a sperm-concentration of less than 10 million/ml, while no evidence for infections or inflammations is given.
2. sera from men which meet the criteria for an inflammation of the seminal ducts on the basis of an ejaculate examination.
3. sera from men with testicular inflammation, detected by means of testicular biopsy.
4. sera from men whose diagnosed testicular and/or seminal duct inflammation was treated with diclofenac, in order to assess if the ER-60 autoantibody titer is correlated with a treatment success.

The invention claimed is:

1. Immunological test for the detection and the specific determination of autoantibodies against testicular antigens which are associated with inflammation-related fertility disorders which are silent or symptomatically progressing inflammations of the testicles, epididymis, seminal ducts or accessory glands of male mammals in a biological sample of a male mammal, which is characterized in that the test comprises binding of these autoantibodies to the specific testicular antigen, wherein autoantibodies against testicular antigens selected from the group consisting of ER-60 autoantibodies and transferrin autoantibodies, are determined, said immunological test comprises the steps of:
providing a biological sample from the male mammal,
providing immobilized protein ER-60 and/or transferrin in recombinant form as a testicular antigen,
contacting said sample of a male mammal with said immobilized specific testicular antigen,
carrying out a quantitative detection of a first value of ER-60 autoantibodies and/or transferrin autoantibodies against testicular antigens ER-60 and/or transferrin present in the biological sample by specific binding to the respective immobilized testicular antigen, respectively, and
comparing said first value with a reference value.

2. Immunological test according to claim 1, wherein the detection of autoantibodies against testicular antigens is performed immunocytochemically, by radioimmunoassay (RIA) or by enzyme-linked-immunosorbent assay (ELISA).

3. Immunological test according to claim 1, wherein the detection of autoantibodies against testicular antigens is performed on a test strip.

4. Immunological test according to claim 1, wherein the test comprises:
bringing into contact a blood sample or other biological specimen from a male mammal, whose content of autoantibodies against testicular antigens is to be determined, with immobilized protein ER-60 and/or transferrin in recombinant form as adsorbed specific testicular antigen
at least one washing step in order to remove non-adsorbed components
and the detection of autoantibodies against testicular antigens bound to the adsorbed antigen using a preparation of IgG antibodies which are species-specific for the male mammal to be investigated and are able to bind species-specifically to the autoantibodies against testicular antigens, and which are labeled with an enzyme peroxidase or alkaline phosphatase.

5. A method of determining the presence of an immunologically-caused and infection-induced infertility in male mammals which are silent or symptomatically progressing inflammations of the testicles, epididymis, seminal ducts or accessory glands comprising the steps of:
providing a biological sample from a male mammal,
providing immobilized protein ER-60 and/or transferrin in recombinant form as a testicular antigen,
contacting said sample of a male mammal with said immobilized specific testicular antigen,
carrying out a quantitative detection of a first value of ER-60 autoantibodies and/or transferrin autoantibodies against testicular antigens ER-60 and/or transferrin present in the biological sample by specific binding to the respective immobilized testicular antigen, respectively, and
comparing said first value with a reference value; wherein an elevated level of said first value as compared to the reference value indicates the presence of the immunologically-caused and infection-induced infertility in the male mammal.

* * * * *